(12) United States Patent
Gomez et al.

(10) Patent No.: US 7,265,200 B2
(45) Date of Patent: Sep. 4, 2007

(54) 1-DESAMINO-8-D-ARGINYL VASOPRESSIN ANALOGS

(75) Inventors: Daniel E. Gomez, Bernal (AR); Daniel F. Alonso, Ranelagh (AR); Giselle V. Ripoll, Quilmes (AR); Santiago Giron, Quilmes (AR)

(73) Assignees: Universidad Nacional De Quilmes, Buenos Aires (AR); Romikin S.A., Buenos Aires (AR)

( * ) Notice: Subject to any disclaimer, the term of this patent is extended or adjusted under 35 U.S.C. 154(b) by 93 days.

(21) Appl. No.: 10/540,841

(22) PCT Filed: Dec. 29, 2003

(86) PCT No.: PCT/US03/41166

§ 371 (c)(1),
(2), (4) Date: Jun. 27, 2005

(87) PCT Pub. No.: WO2004/060389

PCT Pub. Date: Jul. 22, 2004

(65) Prior Publication Data

US 2006/0040857 A1  Feb. 23, 2006

(30) Foreign Application Priority Data

Dec. 27, 2002 (AR) ............... P020105123

(51) Int. Cl.
*C07K 7/16* (2006.01)
*A61K 38/08* (2006.01)

(52) U.S. Cl. ............ 530/315; 514/11; 514/16

(58) Field of Classification Search ............. None
See application file for complete search history.

(56) References Cited

U.S. PATENT DOCUMENTS 3,497,491 A    2/1970  Zaoral et al.
4,148,787 A    4/1979  Mulder et al.
4,261,980 A    4/1981  Cort
4,766,108 A    8/1988  Ali
5,055,448 A    10/1991 Manning et al.
5,486,596 A *  1/1996  Prochazka et al. .......... 530/329

OTHER PUBLICATIONS

Cort et al. Biological and Chiroptical Sequelae of Graded Alkyl Substitutions in the Vasopressin Ring. Molecular Pharmacology. 1976, vol. 12, pp. 313-321.*

Hedenstrom et al. Conformations and Receptor Activity of Desmopressin Analogues . . . Journal of Medicinal Chemistry. May 4, 2002, vol. 45, No. 12, pp. 2501-2511.*

Vilhardt et al. Antidiuretic activity and release of Factor VIII by vasopressin analogues. European Journal of Pharmacology. 1993, vol. 232, pp.223-226.*

Manning et al. Design of vasopressin agonists . . . Peptides 2002, Proceedings of the 27th European Peptide Symposium. 2002, pp. 554-555.*

* cited by examiner

*Primary Examiner*—Jeffrey Edwin Russel
(74) *Attorney, Agent, or Firm*—Sughrue Mion, PLLC

(57) ABSTRACT

Analogs of 1-desamino-8-D-arginyl vasopressin having the formula:

Mpa-Tyr-Phe-X-Y-Cys-Pro-D-Arg-Gly-NH$_2$; or

Mpa-Tyr-Phe-X-Y-Cys-Pro-D-Arg-Gly-NH$_2$, wherein, X and Y are amino acids as defined herein, useful as an anti-diuretic or as an inhibitor of metastasis and cancer cell migration.

14 Claims, No Drawings

1-DESAMINO-8-D-ARGINYL VASOPRESSIN ANALOGS

CROSS-REFERENCE TO RELATED APPLICATIONS

This application is a 371 of PCT/US2003/041166, filed Dec. 29, 2003. This patent application claims the priority benefits of patent application AR P 02-0105123 filed on Dec. 27, 2002. The disclosure of each of the above applications is incorporated herein by reference.

TECHNICAL DESCRIPTION OF THE INVENTION

Analogs of 1-desamino-8-D-arginyl vasopressin. In particular, analogs of 1-desamino-8-D-arginyl vasopressin with substitutions in positions 4 and 5.

TECHNICAL FIELD OF THE INVENTION 1-desamino-8-D-arginyl vasopressin (desmopressin) is an oligopeptide of 8 amino acids. See U.S. Pat. No. 3,497,491 (Zaoral et al); Huguenin et al., *Helv. Chim. Acta,* 49:695 (1966); Zaoral et al., *Coll. Czech. Chem. Commun.,* 32: 1250 (1967). Antidiuretic activity for this peptide is known in the art. See Vavra et al., *Lancet,* 1: 948 (1968). Desmopressin has been used for the treatment of inappropiate secretion of antidiuretic hormone (diabetes insipidus) and childhood enuresis.

Hemostatic and profibrinolytic properties of this oligopeptide are also known in the art. Administration of desmopressin has been associated with an increase in the plasmatic levels of coagulation factor VIII, Von Willebrand factor and tissue-type plasminogen activator. See Mannucci et al., *Br. J. Haematol.,* 30:81-93 (1975). This characteristics of desmopressin have lead to its application in several coagulation disorders, specially during surgeries in patients with hemorragic risk. More recently, the antitumoral action of desmopressin has also been discovered. Use of this oligopeptide was associated to the reduction of metastatic colonization to distant organs from circulating cancer cells and the inhibition of metastasis development in regional lymph nodes after surgical procedures. See AR P990100736; EP 1,031,352; U.S. 200220013262 (Alonso et al); Alonso et al., *Breast Cancer Res. Treat.,* 57:271-275 (1999); Giron et al., *J. Surg. Oncol.,* 81: 38-44 (2002).

The existence of desmopressin analogs with biological activities equal or higher than desmopressin is also known in the art. These analogs have been developed, for example, from the methylation or substitution of one or more amino acids from the peptidic chain of desmopressin or its precursor, vasopressin. See Loukoti, *J. Pept, Sci* 6(3): 123-9 (2000); Kihlberg et al., *J. Med. Chem.,* 38 (1): 161-9 (1995); Barth et al., *Eur J. Pharmacol.,* 232(2-3):223-6 (1993); Barth, *J. Recept. Res.,* 13(1-4): 305-11 (1993); Lammek et al., *J. Med. Chem.,* 32(1):244-7 (1989); U.S. Pat. No. 4,876,243 (Marshall et al). However, at the present it has not been described in the art the simultaneous substitution of amino acids in positions 4 and 5 of the peptidic chain of desmopressin combined with the elimination of the disulfide bond between positions 1 and 6.

DESCRIPTION OF THE INVENTION

The present invention claims analogs of 1-desamino-8-D-arginyl vasopressin not known at the present in the art. Some of the oligopeptides described herein exhibit a high capacity to inhibit metastasis and cancerous cells migation. Two of the additional advantages of the oligopeptides described herein are their easiness to synthesize and their relative low cost of production.

The oligopeptides claimed according to the present invention were synthesized by the method of Houghten (tea bags method). See Houghten, *Proc. Natl. Acad. Sci. USA,* 82:5131-35 (1985); Houghten et al, *Int. J. Peptide Protein Res.,* 27: 673-678 (1985); U.S. Pat. No. 5,486,596 (Prochazka et al). By using Houghten's method, peptidic synthesis is carried out utilizing small porous bags made of polypropylene (tea bags) containing amino acids bound to a resin. The bags are submerged in solutions containing activated amino acids to induce the coupling of the amino acids in solution to the amino acids bound to the resin. During this stage of the process, amino acids bound to the resin are washed and unprotected in order to favor its coupling to the activated amino acids in solution. The polypropylene bag is extracted from the solution of the first reaction and submerged into a second solution containing other activated amino acids, in order to incorporate, in this way, additional amino acids to the peptidic chain. The process is repeated several times to obtain the peptide of interest. This procedure, together with its variations, are known in the art. See Grant, G., Ed., "Synthetic Peptides" (W.H. Freeman & Co., New York, 1992) pages 78-142. In one of the embodiments of the present invention the analogs of 1-desamino-8-D-arginyl vasopressin are characterized by the following general formula:

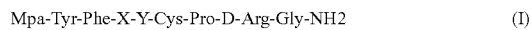

Mpa-Tyr-Phe-X-Y-Cys-Pro-D-Arg-Gly-NH2 (I)

In another of the embodiments of the present invention, the analogs of 1-desamino-8-D-arginyl vasopressin claimed are characterized for having a disulphide bond between Mpa group in position 1 and the cysteine in position 6. In these cases, the analogs of 1-desamino-8-D-arginyl vasopressin are characterized by the general formula:

Mpa-Tyr-Phe-X-Y-Cys-Pro-D-Arg-Gly-NH2 (II)

Preferably, X is a weak polar or a non polar amino acid. Most preferably, the amino acid is asparagine or glutamine when a weak polar amino acid is used, or alanine, valine, leucine, or isoleucine, when a non polar amino acid is used. Preferably, Y is a weak polar or a non polar amino acid. Most preferably, the amino acid is asparagine or glutamine when a weak polar amino acid is used, or valine, leucine or isoleucine, when a non polar amino acid is used.

As employed in the present description, "Mpa" means the radical of 1-mercaptopropanoic acid of formula SH—$CH_2$—$CH_2$—COOH.

General Procedures

The peptides claimed in the present invention were synthesized according with the procedures indicated as follows:
1. Assembling Peptides were assembled by the use of a resin of methylbenzyhydrilamine using Boc/Bencil techniques according with the following protocol:

1) Polypropylene porous bags were filled with a methylbenzyhydrilamine resin. Then, the bags were put in a Nalgene™ bottle and dychloromethane was added until covering them. The Nalgene™ bottle was then agitated for five minutes to allow resin saturation. Dychloromethane solution was extracted.

2) Polypropylene bags from the previous step were washed three times with dychloromethane containing 5% of diisopropylamine. Each wash was two minutes long. The polypropylene bags were then washed three times with dychloromethane for 1 minute each time to eliminate the excess of diisopropylamine.

3) Polypropylene bags from the previous step were put into a Nalgene™ bottle containing a solution of the amino acid of interest in dychloromethane. Afterwards, an equal quantity of diisopropylcarbodimide dissolved in dychloromethane was added to activate the coupling of the amino acid dissolved to the methylbenzyhydrilamine resin. The Nalgene™ bottle was agitated for 1 hour until completion of the reaction.

4) The reaction solution from the previous step was discarded. Polypropylene bags from the previous step were washed with N,N-dimethylformamide twice for one minute each to eliminate the excess of amino acids and other secondary products.

5) Polypropylene bags from the previous step were washed with dychloromethane twice for one minute each to eliminate the excess of N,N-dimethylformamide. The protective group N-α-ter-butylxicarbonyl (N-a-t-Boc) was removed by acidlysis using a 55% solution of trifluoracetic acid in dychloromethane. Polypropylene bags were exposed to the trifluoracetic acid solution for 30 minutes. This reaction resulted in the trifluoracetic salt of the α-amino group.

6) Polypropylene bags from the previous step were washed successively with: a) dychloromethane, once for one minute, b) isopropanol, twice, for one minute each time and c) dychloromethane, once for one minute.

The previous protocol was repeated for each one of the amino acids in such an order as to yield the desmopressin analogs described by the present invention.

2. Extraction

The peptides assembled according with the previous procedure were cleaved from the resin of methylbenzyhidrilamine according with the following protocol:

1) The peptide bound to the resin from the previous procedure was subjected to the action of fluorhydric acid in the presence of anisole at 0° C. during one hour to liberate such peptide from the resin.

2) Fluorhydric acid from the reaction mix was removed by a nitrogen flux at 0° C. during one hour.

3) Resin and peptide from the previous step were washed twice with ether.

4) The peptide was extracted from the reaction mix from the previous step with a 10% solution of acetic acid. This process was carried out twice.

5) Extraction solutions from the previous step containing the peptide were lyophilized.

6) Peptide was stored in a nitrogen atmosphere.

The previous protocol was repeated for each one of the peptides described in the present invention.

3. Purification

The peptides obtained according with the previous procedure were purified by reverse phase high performance liquid chromatography using a $C_{18}$ column. As solvents were employed: a) a water solution containing 0.1% trifluoracetic acid and b) an acetonitrile solution containing 0.1% trifluoroacetic acid. Peptides purified according with this procedure were lyophilized afterwards.

The previous protocol was repeated for each one of the peptides described in the present invention.

4. Formation of the disulphide bond

Linearized peptides obtained according with the previous procedure were dissolved in water until obtaining a solution of initial reaction of 5 mg/ml. A 1 M solution of $NH_4HCO_3$ was slowly added to the reaction solution until obtaining a slightly basic concentration of pH 7,5. Then, a 1,5% solution of $H_2O_2$ was slowly added to the reaction solution stirring gently. The resulting reaction solution was periodically analyzed by mass spectroscopy to verify the degree of formation of the disulphide bonds. After formation of the disulphide bonds, pH of the reaction solution was changed to pH 4 with $CH_3COOH$. The peptides with disulphide bonds resulting from this procedure were purified by reverse phase high performance liquid chromatography.

The previous protocol was repeated for each one of the peptides described in the present invention.

EXAMPLE 1

Analogs of 1-desamino-8-D-arginyl Vasopressin without Di-sulphur Bonds Between Positions 1 and 6

In accordance with general procedures 1, 2 and 3 the following desmopressin analogs were synthesized:

1) 3-mercaptopropionyl-L-tirosyl-L-phenylalanyl-L-alanyl-L-asparagyl-L-cysteil-L-prolyl-D-argyl-L-glicynamide:

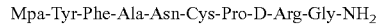
Mpa-Tyr-Phe-Ala-Asn-Cys-Pro-D-Arg-Gly-NH$_2$ 2) 3-mercaptopropionyl-L-tirosyl-L-phenylalanyl-L-alanyl-L-glutamyl-L-cysteil-L-prolyl-D-argyl-L-glicynamide:

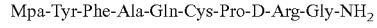
Mpa-Tyr-Phe-Ala-Gln-Cys-Pro-D-Arg-Gly-NH$_2$ 3) 3-mercaptopropionyl-L-tirosyl-L-phenylalanyl-L-alanyl-L-isoleucyl-L-cysteil-L-prolyl-D-argyl-L-glicynamide:

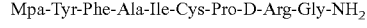
Mpa-Tyr-Phe-Ala-Ile-Cys-Pro-D-Arg-Gly-NH$_2$ 4) 3-mercaptopropionyl-L-tirosyl-L-phenylalanyl-L-alanyl-L-leucyl-L-cysteil-L-prolyl-D-argyl-L-glicynamide:

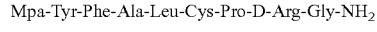
Mpa-Tyr-Phe-Ala-Leu-Cys-Pro-D-Arg-Gly-NH$_2$ 5) 3-mercaptopropionyl-L-tirosyl-L-phenylalanyl-L-alanyl-L-valyl-L-cysteil-L-prolyl-D-argyl-L-glicynamide:

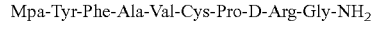
Mpa-Tyr-Phe-Ala-Val-Cys-Pro-D-Arg-Gly-NH$_2$ 6) 3-mercaptopropionyl-L-tirosyl-L-phenylalanyl-L-asparagyl-L-asparagyl-L-cysteil-L-prolyl-D-argyl-L-glicynamide:

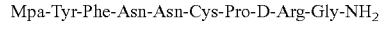
Mpa-Tyr-Phe-Asn-Asn-Cys-Pro-D-Arg-Gly-NH$_2$ 7) 3-mercaptopropionyl-L-tirosyl-L-phenylalanyl-L-asparagyl-L-glutaminyl-L-cysteil-L-prolyl-D-argyl-L-glicynamide:

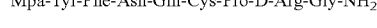
Mpa-Tyr-Phe-Asn-Gln-Cys-Pro-D-Arg-Gly-NH$_2$ 8) 3-mercaptopropionyl-L-tirosyl-L-phenylalanyl-L-asparagyl-L-isoleucyl-L-cysteil-L-prolyl-D-argyl-L-glicynamide:

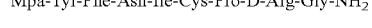
Mpa-Tyr-Phe-Asn-Ile-Cys-Pro-D-Arg-Gly-NH$_2$ 9) 3-mercaptopropionyl-L-tirosyl-L-phenylalanyl-L-asparagyl-L-leucyl-L-cysteil-L-prolyl-D-argyl-L-glicynamide:

Mpa-Tyr-Phe-Asn-Leu-Cys-Pro-D-Arg-Gly-NH$_2$ 10) 3-mercaptopropionyl-L-tirosyl-L-phenylalanyl-L-asparagyl-L-valyl-L-cysteil-L-prolyl-D-argyl-L-glicynamide:

Mpa-Tyr-Phe-Asn-Val-Cys-Pro-D-Arg-Gly-NH$_2$ 11) 3-mercaptopropionyl-L-tirosyl-L-phenylalanyl-L-glutaminyl-L-asparagyl-L-cysteil-L-prolyl-D-argyl-L-glicynamide:

Mpa-Tyr-Phe-Gln-Asp-Cys-Pro-D-Arg-Gly-NH$_2$ 12) 3-mercaptopropionyl-L-tirosyl-L-phenylalanyl-L-glutaminyl-L-glutaminyl-L-cysteil-L-prolyl-D-argyl-L-glicynamide:

Mpa-Tyr-Phe-Gln-Gln-Cys-Pro-D-Arg-Gly-NH$_2$ 13) 3-mercaptopropionyl-L-tirosyl-L-phenylalanyl-L-glutaminyl-L-isoleucyl-L-cysteil-L-prolyl-D-argyl-L-glicynamide:

Mpa-Tyr-Phe-Gln-Ile-Cys-Pro-D-Arg-Gly-NH$_2$ 14) 3-mercaptopropionyl-L-tirosyl-L-phenylalanyl-L-glutaminyl-L-leucyl-L-cysteil-L-prolyl-D-argyl-L-glicynamide:

Mpa-Tyr-Phe-Gln-Leu-Cys-Pro-D-Arg-Gly-NH$_2$ 15) 3-mercaptopropionyl-L-tirosyl-L-phenylalanyl-L-glutaminyl-L-valyl-L-cysteil-L-prolyl-D-argyl-L-glicynamide:

Mpa-Tyr-Phe-Gln-Val-Cys-Pro-D-Arg-Gly-NH$_2$ 16) 3-mercaptopropionyl-L-tirosyl-L-phenylalanyl-L-isoleucyl-L-asparagyl-L-cysteil-L-prolyl-D-argyl-L-glicynamide:

Mpa-Tyr-Phe-Ile-Asn-Cys-Pro-D-Arg-Gly-NH$_2$ 17) 3-mercaptopropionyl-L-tirosyl-L-phenylalanyl-L-isoleucyl-L-glutaminyl-L-cysteil-L-prolyl-D-argyl-L-glicynamide:

Mpa-Tyr-Phe-Ile-Gln-Cys-Pro-D-Arg-Gly-NH$_2$ 18) 3-mercaptopropionyl-L-tirosyl-L-phenylalanyl-L-isoleucyl-L-isoleucyl-L-cysteil-L-prolyl-D-argyl-L-glicynamide:

Mpa-Tyr-Phe-Ile-Ile-Cys-Pro-D-Arg-Gly-NH$_2$ 19) 3-mercaptopropionyl-L-tirosyl-L-phenylalanyl-L-isoleucyl-L-leucyl-L-cysteil-L-prolyl-D-argyl-L-glicynamide:

Mpa-Tyr-Phe-Ile-Leu-Cys-Pro-D-Arg-Gly-NH$_2$ 20) 3-mercaptopropionyl-L-tirosyl-L-phenylalanyl-L-isoleucyl-L-valyl-L-cysteil-L-prolyl-D-argyl-L-glicynamide:

Mpa-Tyr-Phe-Ile-Val-Cys-Pro-D-Arg-Gly-NH$_2$ 21) 3-mercaptopropionyl-L-tirosyl-L-phenylalanyl-L-leucyl-L-asparagyl-L-cysteil-L-prolyl-D-argyl-L-glicynamide:

Mpa-Tyr-Phe-Leu-Asn-Cys-Pro-D-Arg-Gly-NH$_2$ 22) 3-mercaptopropionyl-L-tirosyl-L-phenylalanyl-L-leucyl-L-glutaminyl-L-cysteil-L-prolyl-D-argyl-L-glicynamide:

Mpa-Tyr-Phe-Leu-Gln-Cys-Pro-D-Arg-Gly-NH$_2$ 23) 3-mercaptopropionyl-L-tirosyl-L-phenylalanyl-L-leucyl-L-isoleucyl-L-cysteil-L-prolyl-D-argyl-L-glicynamide:

Mpa-Tyr-Phe-Leu-Ile-Cys-Pro-D-Arg-Gly-NH$_2$ 24) 3-mercaptopropionyl-L-tirosyl-L-phenylalanyl-L-leucyl-L-leucyl-L-cysteil-L-prolyl-D-argyl-L-glicynamide:

Mpa-Tyr-Phe-Leu-Leu-Cys-Pro-D-Arg-Gly-NH$_2$ 25) 3-mercaptopropionyl-L-tirosyl-L-phenylalanyl-L-leucyl-L-valyl-L-cysteil-L-prolyl-D-argyl-L-glicynamide:

Mpa-Tyr-Phe-Leu-Val-Cys-Pro-D-Arg-Gly-NH$_2$ 26) 3-mercaptopropionyl-L-tirosyl-L-phenylalanyl-L-valyl-L-asparagyl-L-cysteil-L-prolyl-D-argyl-L-glicynamide:

Mpa-Tyr-Phe-Val-Asn-Cys-Pro-D-Arg-Gly-NH$_2$ 27) 3-mercaptopropionyl-L-tirosyl-L-phenylalanyl-L-valyl-L-glutaminyl-L-cysteil-L-prolyl-D-argyl-L-glicynamide:

Mpa-Tyr-Phe-Val-Gln-Cys-Pro-D-Arg-Gly-NH$_2$ 28) 3-mercaptopropionyl-L-tirosyl-L-phenylalanyl-L-valyl-L-isoleucyl-L-cysteil-L-prolyl-D-argyl-L-glicynamide:

Mpa-Tyr-Phe-Val-Ile-Cys-Pro-D-Arg-Gly-NH$_2$ 29) 3-mercaptopropionyl-L-tirosyl-L-phenylalanyl-L-valyl-L-leucyl-L-cysteil-L-prolyl-D-argyl-L-glicynamide:

Mpa-Tyr-Phe-Val-Leu-Cys-Pro-D-Arg-Gly-NH$_2$ 30) 3-mercaptopropionyl-L-tirosyl-L-phenylalanyl-L-valyl-L-valyl-L-cysteil-L-prolyl-D-argyl-L-glicynamide:

Mpa-Tyr-Phe-Val-Val-Cys-Pro-D-Arg-Gly-NH$_2$

EXAMPLE 2

Analogs of 1-desamin-8-D-arginyl Vasopressin with Di-sulphur Bonds Between Positions 1 and 6

In accordance with general procedures 1, 2, 3 and 4 the following desmopressin analogs were synthesized:

1) 1-(3-mercaptopropanoic acid)-4-L-alanyl-5-L-asparagyl-8-D-arginyl vasopressin:

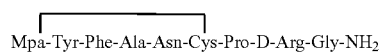

2) 1-(3-mercaptopropanoic acid)-4-L-alanyl-5-L-glutaminyl-8-D-arginyl vasopressin:

3) 1-(3-mercaptopropanoic acid)-4-L-alanyl-5-L-isoleucyl-8-D-arginyl vasopressin:

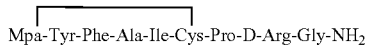
Mpa-Tyr-Phe-Ala-Ile-Cys-Pro-D-Arg-Gly-NH₂

4) 1-(3-mercaptopropanoic acid)-4-L-alanyl-5-L-leucyl-8-D-arginyl vasopressin:

Mpa-Tyr-Phe-Ala-Leu-Cys-Pro-D-Arg-Gly-NH₂

5) 1-(3-mercaptopropanoic acid)-4-L-alanyl-5-L-valyl-8-D-arginyl vasopressin:

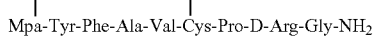
Mpa-Tyr-Phe-Ala-Val-Cys-Pro-D-Arg-Gly-NH₂

6) 1-(3-mercaptopropanoic acid)-4-L-asparagyl-5-L-asparagyl-8-D-arginyl vasopressin:

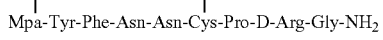
Mpa-Tyr-Phe-Asn-Asn-Cys-Pro-D-Arg-Gly-NH₂

7) 1-(3-mercaptopropanoic acid)-4-L-asparagyl-5-L-glutaminyl-8-D-arginyl vasopressin:

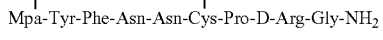
Mpa-Tyr-Phe-Asn-Gln-Cys-Pro-D-Arg-Gly-NH₂

8) 1-(3-mercaptopropanoic acid)-4-L-asparagyl-5-L-isoleucyl-8-D-arginyl vasopressin:

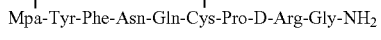
Mpa-Tyr-Phe-Asn-Ile-Cys-Pro-D-Arg-Gly-NH₂

9) 1-(3-mercaptopropanoic acid)-4-L-asparagyl-5-L-leucyl-8-D-arginyl vasopressin:

Mpa-Tyr-Phe-Asn-Leu-Cys-Pro-D-Arg-Gly-NH₂

10) 1-(3-mercaptopropanoic acid)-4-L-asparagyl-5-L-valyl-8-D-arginyl vasopressin:

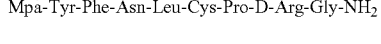
Mpa-Tyr-Phe-Asn-Val-Cys-Pro-D-Arg-Gly-NH₂

11) 1-(3-mercaptopropanoic acid)-4-L-glutaminyl-5-L-glutaminyl-8-D-arginyl vasopressin:

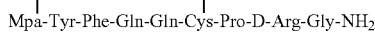
Mpa-Tyr-Phe-Gln-Gln-Cys-Pro-D-Arg-Gly-NH₂

12) 1-(3-mercaptopropanoic acid)-4-L-glutaminyl-5-L-isoleucyl-8-D-arginyl vasopressin:

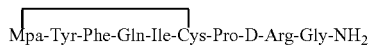
Mpa-Tyr-Phe-Gln-Ile-Cys-Pro-D-Arg-Gly-NH₂

13) 1-(3-mercaptopropanoic acid)-4-L-glutaminyl-5-L-leucyl-8-D-arginyl vasopressin:

Mpa-Tyr-Phe-Gln-Leu-Cys-Pro-D-Arg-Gly-NH₂

14) 1-(3-mercaptopropanoic acid)-4-L-glutaminyl-5-L-valyl-8-D-arginyl vasopressin:

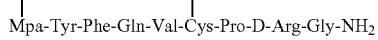
Mpa-Tyr-Phe-Gln-Val-Cys-Pro-D-Arg-Gly-NH₂

15) 1-(3-mercaptopropanoic acid)-4-L-isoleucyl-5-L-asparagyl-8-D-arginyl vasopressin:

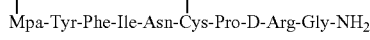
Mpa-Tyr-Phe-Ile-Asn-Cys-Pro-D-Arg-Gly-NH₂

16) 1-(3-mercaptopropanoic acid)-4-L-isoleucyl-5-L-glutaminyl-8-D-arginyl vasopressin:

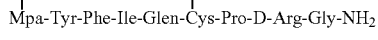
Mpa-Tyr-Phe-Ile-Glen-Cys-Pro-D-Arg-Gly-NH₂

17) 1-(3-mercaptopropanoic acid)-4-L-isoleucyl-5-L-isoleucyl-8-D-arginyl vasopressin:

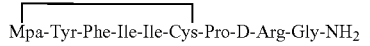
Mpa-Tyr-Phe-Ile-Ile-Cys-Pro-D-Arg-Gly-NH₂

18) 1-(3-mercaptopropanoic acid)-4-L-isoleucyl-5-L-leucyl-8-D-arginyl vasopressin:

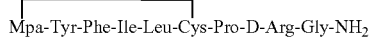
Mpa-Tyr-Phe-Ile-Leu-Cys-Pro-D-Arg-Gly-NH₂

19) 1-(3-mercaptopropanoic acid)-4-L-isoleucyl-5-L-valyl-8-D-arginyl vasopressin:

Mpa-Tyr-Phe-Ile-Val-Cys-Pro-D-Arg-Gly-NH₂

20) 1-(3-mercaptopropanoic acid)-4-L-leucyl-5-L-asparagyl-8-D-arginyl vasopressin:

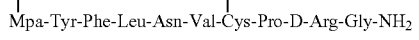
Mpa-Tyr-Phe-Leu-Asn-Val-Cys-Pro-D-Arg-Gly-NH₂

21) 1-(3-mercaptopropanoic acid)-4-L-leucyl-5-L-glutaminyl-8-D-arginyl vasopressin:

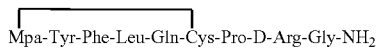
Mpa-Tyr-Phe-Leu-Gln-Cys-Pro-D-Arg-Gly-NH$_2$ 22) 1-(3-mercaptopropanoic acid)-4-L-leucyl-5-L-isoleucyl-8-D-arginyl vasopressin:

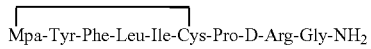
Mpa-Tyr-Phe-Leu-Ile-Cys-Pro-D-Arg-Gly-NH$_2$ 23) 1-(3-mercaptopropanoic acid)-4-L-leucyl-5-L-leucyl-8-D-arginyl vasopressin:

Mpa-Tyr-Phe-Leu-Leu-Cys-Pro-D-Arg-Gly-NH$_2$ 24) 1-(3-mercaptopropanoic acid)-4-L-leucyl-5-L-valyl-8-D-arginyl vasopressin:

Mpa-Tyr-Phe-Leu-Val-Cys-Pro-D-Arg-Gly-NH$_2$ 25) 1-(3-mercaptopropanoic acid)-4-L-valyl-5-L-asparagyl-8-D-arginyl vasopressin:

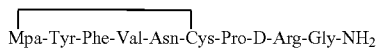
Mpa-Tyr-Phe-Val-Asn-Cys-Pro-D-Arg-Gly-NH$_2$ 26) 1-(3-mercaptopropanoic acid)-4-L-valyl-5-L-glutaminyl-8-D-arginyl vasopressin:

Mpa-Tyr-Phe-Val-Gln-Cys-Pro-D-Arg-Gly-NH$_2$ 27) 1-(3-mercaptopropanoic acid)-4-L-valyl-5-L-isoleucyl-8-D-arginyl vasopressin:

Mpa-Tyr-Phe-Val-Ile-Cys-Pro-D-Arg-Gly-NH$_2$ 28) 1-(3-mercaptopropanoic acid)-4-L-valyl-5-L-leucyl-8-D-arginyl vasopressin:

Mpa-Tyr-Phe-Val-Leu-Cys-Pro-D-Arg-Gly-NH$_2$ 29) 1-(3-mercaptopropanoic acid)-4-L-valyl-5-L-valyl-8-D-arginyl vasopressin:

Mpa-Tyr-Phe-Val-Val-Cys-Pro-D-Arg-Gly-NH$_2$

The present invention has been described in some detail and exemplified to facilitate its understanding and reproducibility. Certain changes in the form and detail can be made by anyone skilled in the art without departing from the true object and scope of the claims of the present invention. All the publications quoted herein are incorporated in their totality as references to the description of the invention.

What is claimed is:

1. An analog of 1-desamino-8-D-arginyl vasopressin, wherein said analog has the following general formula:

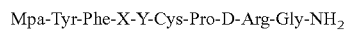
Mpa-Tyr-Phe-X-Y-Cys-Pro-D-Arg-Gly-NH$_2$ wherein,
Mpa is a radical of 1-mercaptopropanoic acid of the formula SH—CH$_2$—CH$_2$—COOH;
X is an amino acid selected from the group consisting of alanine, asparagine, glutamine, isoleucine, leucine and valine; and
Y is an amino acid selected from the group consisting of glutamine, isoleucine, leucine and valine,
with the proviso that
when X is asparagine or glutamine, Y is not glutamine.

2. The analog of 1-desamino-8-D-arginyl vasopressin as claimed in claim 1, wherein X is alanine and Y is selected from the group consisting of glutamine, isoleucine, leucine and valine.

3. The analog of 1-desamino-8-D-arginyl vasopressin as claimed in claim 1, wherein X is asparagine and Y is selected from the group consisting of isoleucine, leucine and valine.

4. The analog of 1-desamino-8-D-arginyl vasopressin as claimed in claim 1, wherein X is glutamine and Y is selected from the group consisting of isoleucine, leucine and valine.

5. The analog of 1-desamino-8-D-arginyl vasopressin as claimed in claim 1, wherein X is isoleucine and Y is selected from the group consisting of glutamine, isoleucine, leucine and valine.

6. The analog of 1-desamino-8-D-arginyl vasopressin as claimed in claim 1, wherein X is leucine and Y is selected from the group consisting of glutamine, isoleucine, leucine and valine.

7. The analog of 1-desamino-8-D-arginyl vasopressin as claimed in claim 1, wherein X is valine and Y is selected from the group consisting of glutamine, isoleucine, leucine and valine.

8. An analog of 1-desamino-8-D-arginyl vasopressin, wherein said analog has the following general formula:

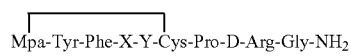
Mpa-Tyr-Phe-X-Y-Cys-Pro-D-Arg-Gly-NH$_2$ wherein,
Mpa is a radical of 1-mercaptopropanoic acid of the formula SH—CH$_2$—CH$_2$—COOH;
X is an amino acid selected from the group consisting of alanine, asparagine, glutamine, isoleucine, leucine and valine; and
Y is an amino acid selected from the group consisting of glutamine, isoleucine, leucine and valine,
with the proviso that
when X is asparagine or glutamine, Y is not glutamine.

9. The analog of 1-desamino-8-D-arginyl vasopressin as claimed in claim 8, wherein X is alanine and Y is selected from the group consisting of glutamine, isoleucine, leucine and valine.

10. The analog of 1-desamino-8-D-arginyl vasopressin as claimed in claim 8, wherein X is asparagine and Y is selected from the group consisting of isoleucine, leucine and valine.

11. The analog of 1-desamino-8-D-arginyl vasopressin as claimed in claim 8, wherein X is glutamine and Y is selected from the group consisting of isoleucine, leucine and valine.

12. The analog of 1-desamino-8-D-arginyl vasopressin as claimed in claim 8, wherein X is isoleucine and Y is selected from the group consisting of glutamine, isoleucine, leucine and valine.

13. The analog of 1-desamino-8-D-arginyl vasopressin as claimed in claim 8, wherein X is leucine and Y is selected from the group consisting of glutamine, isoleucine, leucine and valine.

14. The analog of 1-desamino-8-D-arginyl vasopressin as claimed in claim 8, wherein X is valine and Y is selected from the group consisting of glutamine, isoleucine, leucine and valine.

\* \* \* \* \*